US011408806B2

(12) United States Patent
Sun et al.

(10) Patent No.: US 11,408,806 B2
(45) Date of Patent: Aug. 9, 2022

(54) SYSTEM AND METHOD FOR MONITORING CRACK PROPAGATION OF TRANSPARENT ROCK SPECIMEN

(71) Applicant: SHANDONG UNIVERSITY OF SCIENCE AND TECHNOLOGY, Qingdao (CN)

(72) Inventors: Wenbin Sun, Qingdao (CN); Houqian Du, Qingdao (CN); Yanchao Xue, Qingdao (CN); Jianli Shao, Qingdao (CN); Liming Yin, Qingdao (CN); Fei Zhou, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 222 days.

(21) Appl. No.: 16/976,715

(22) PCT Filed: Aug. 24, 2018

(86) PCT No.: PCT/CN2018/102186
§ 371 (c)(1),
(2) Date: Aug. 28, 2020

(87) PCT Pub. No.: WO2019/237509
PCT Pub. Date: Dec. 19, 2019

(65) Prior Publication Data
US 2020/0408656 A1     Dec. 31, 2020

(30) Foreign Application Priority Data
Jun. 13, 2018   (CN) .......................... 201810604310.2

(51) Int. Cl.
*G01N 3/06*     (2006.01)
*G01N 3/08*     (2006.01)

(52) U.S. Cl.
CPC ............... *G01N 3/068* (2013.01); *G01N 3/08* (2013.01); *G01N 2203/0019* (2013.01); *G01N 2203/0066* (2013.01)

(58) Field of Classification Search
CPC .. G01N 3/068; G01N 3/08; G01N 2203/0019; G01N 2203/0066
(Continued)

(56) References Cited

U.S. PATENT DOCUMENTS 6,634,185 B2 * 10/2003 Chomay ................. B29C 73/26
                                                          264/36.21
2014/0210946 A1 * 7/2014 Hsiao ................... H04N 13/254
                                                          348/46

FOREIGN PATENT DOCUMENTS

CN       1536350 A     10/2004
CN     101608905 A     12/2009
(Continued)

OTHER PUBLICATIONS

International Search Report, PCT/CN2018/102186 [ISA/CN] dated Mar. 11, 2019.

*Primary Examiner* — Octavia Davis Hollington
(74) *Attorney, Agent, or Firm* — Daniel J. Chalker; Edwin S. Flores; Chalker Flores, LLP

(57) ABSTRACT

A system and method for monitoring crack propagation of a transparent rock specimen monitors a breakage process of a specimen loading process. In the system and method for monitoring crack propagation of a transparent rock specimen, under the condition of no contact with a rock specimen, intensity changes of laser light passing through the transparent rock specimen in a loading state are determined, such that a computer (5) forms, according to laser intensity change data, a three-dimensional diagram of crack propagation of the transparent rock specimen (4) in a continuously loaded state at a plurality of set time points. This is used to
(Continued)

analyze a breakage starting point and a crack propagation path and process of the transparent rock specimen (4) in the loading state, and achieve the purpose of qualitative analysis of the rock specimen.

15 Claims, 3 Drawing Sheets

(58) Field of Classification Search
USPC .......................................................... 73/799
See application file for complete search history.

(56) References Cited

FOREIGN PATENT DOCUMENTS

| | | | | | |
|---|---|---|---|---|---|
| CN | 102680496 | A | | 9/2012 | |
| CN | 104916192 | A | | 9/2015 | |
| CN | 106885770 | A | | 6/2017 | |
| CN | 107328625 | A | * | 11/2017 | ............... C03C 1/00 |
| CN | 107807135 | A | | 3/2018 | |
| CN | 108956274 | A | * | 12/2018 | |
| CN | 110686971 | B | * | 10/2020 | |
| CN | 114324121 | A | * | 4/2022 | |
| JP | 2013091578 | A | | 5/2013 | |
| KR | 20100068743 | A | * | 6/2010 | |

\* cited by examiner

SYSTEM AND METHOD FOR MONITORING CRACK PROPAGATION OF TRANSPARENT ROCK SPECIMEN

CROSS-REFERENCE TO RELATED APPLICATIONS

This application is the National Stage of International Application No. PCT/CN2018/102186, filed on Aug. 24, 2020 claiming the priority of CN 201810604310.2, filed on Jun. 13, 2020, the content of each of which is incorporated by reference herein.

TECHNICAL FIELD OF THE INVENTION

The present invention relates to the technical field of uniaxial compression tests of rock, and in particular, to a system and method for monitoring crack propagation of a transparent rock specimen.

BACKGROUND OF THE INVENTION

Uniaxial compression tests of rock are the basis of solving practical engineering problems, and the key to dealing with practical engineering problems is to study the breakage limit and process of rock. Most practical engineering problems are dealt with by similar models, so as to obtain similar laws to solve the problems. The current studies on breakage of rock in loading processes are mostly performed by infrared testing, acoustic emission, CT scanning, etc. Infrared testing is the observation of the outer surface of a specimen, which cannot test internal changes. Acoustic emission testing is greatly affected by environmental noise, etc., so that detailed information on cracks cannot be given. CT scanning is discontinuous testing, which can only give intermittent results for rock breakage.

SUMMARY OF THE INVENTION

The present invention provides a system and method for monitoring crack propagation of a transparent rock specimen, so as to solve the technical problem that a breakage process of a specimen in a loading process cannot be monitored at present.

The present invention provides a system for monitoring crack propagation of a transparent rock specimen, including a uniaxial rock loading device, where a transparent rock specimen is arranged on a loading base of the uniaxial rock loading device, and a loading head of the uniaxial rock loading device is arranged above the transparent rock specimen. The system for monitoring crack propagation of a transparent rock specimen further includes laser emitters for emitting laser light to the transparent rock specimen, laser receiving plates for receiving the laser light emitted by the laser emitters and a computer for acquiring and processing laser intensity data. A laser emitter is separately arranged at a left side and a front side of the uniaxial rock loading device, respectively; a laser receiving plate is separately arranged at a right side and a rear side of the uniaxial rock loading device. A direction of the laser light emitted by the laser emitter is perpendicular to a surface of the laser receiving plate, and the laser light passes through the transparent rock specimen; and the computer is in signal connection with the two laser receiving plates.

Further, the laser receiving plate includes a substrate, a plurality of photosensitive sensors are uniformly arranged on the substrate, and the computer is in signal connection with the photosensitive sensors.

Further, the laser receiving plate further includes a supporting frame, the substrate is hinged in the supporting frame, the supporting frame is provided with an adjusting screw, and a tail end of the adjusting screw can press or be separated from the substrate by rotating the adjusting screw.

Further, the laser emitter includes a plurality of laser emission sources, and laser light emitted by the plurality of laser emission sources forms a laser beam which covers the transparent rock specimen.

Further, the transparent rock specimen is composed of epoxy resin adhesives and polymethyl methacrylate (PMMA) particles by mixing.

The present invention further provides a method for monitoring crack propagation of a transparent rock specimen, which applies the foregoing system for monitoring crack propagation of a transparent rock specimen. The method includes the following steps:

step 1: placing a transparent rock specimen on a loading base of a uniaxial rock loading device, arranging a laser emitter separately at a left side and a front side of the uniaxial rock loading device, arranging a laser receiving plate separately at a right side and a rear side of the uniaxial rock loading device, and connecting the laser receiving plate with a computer;

step 2: aligning an emitting end of each laser emitter with the transparent rock specimen, starting the laser emitter to emit laser light to the transparent rock specimen, rotating a substrate of each laser receiving plate, so that a laser direction is perpendicular to a surface of the substrate, and rotating an adjusting screw so that a tail end of the adjusting screw presses the substrate;

step 3: emitting, by the left laser emitter, laser light to the transparent rock specimen; after the laser light passes through the transparent rock specimen, recording laser intensity by the right laser receiving plate; emitting, by the front laser emitter, laser light to the transparent rock specimen; after the laser light passes through the transparent rock specimen, recording laser intensity by the rear laser receiving plate, and acquiring, by the computer, initial laser intensity data for the transparent rock specimen in an unloaded state through the two laser receiving plates;

step 4: starting the uniaxial rock loading device, uniaxially loading the transparent rock specimen by the loading head and the loading base, and continuously emitting laser light to the transparent rock specimen by the left laser emitter while loading; after the laser light passes through the transparent rock specimen, continuously recording laser intensity by the right laser receiving plate; continuously emitting laser light to the transparent rock specimen by the front laser emitter; after the laser light passes through the transparent rock specimen, continuously recording laser intensity by the rear laser receiving plate, and continuously acquiring, by the computer, laser intensity data of the transparent rock specimen in a continuously loaded state through the two laser receiving plates; and step 5: according to the acquired initial laser intensity data in the unloaded state and the acquired laser intensity data in the continuously loaded state, processing, by the computer, to form a three-dimensional diagram of crack propagation of the transparent rock specimen at a plurality of set time points in the continuously loaded state.

Compared with the prior art, the system and method for monitoring crack propagation of a transparent rock specimen according to the present invention have the following features and advantages:

In the system and method for monitoring crack propagation of a transparent rock specimen, under the condition of no contact with a rock specimen, intensity changes of laser light passing through the transparent rock specimen in a loading state are determined, such that a computer forms, according to laser intensity change data, a three-dimensional diagram of crack propagation of the transparent rock specimen in a continuously loaded state at a plurality of set time points. This is used to analyze a breakage starting point and a crack propagation path and process of the transparent rock specimen in the loading state, and achieve the purpose of qualitative analysis of the rock specimen.

The features and advantages of the present invention will become clearer with reference to accompanying drawings and specific implementations of the present invention.

BRIEF DESCRIPTION OF THE DRAWINGS

To describe the technical solutions in the examples of the present invention or in the prior art more clearly, the following briefly describes the accompanying drawings required for describing the examples or the prior art. Apparently, the accompanying drawings in the following description show some examples of the present invention, and a person of ordinary skill in the art may still derive other accompanying drawings from these accompanying drawings without creative efforts.

In the figure: 1. uniaxial rock loading device, 11. loading head, 12. loading base, 2. laser emitter, 3. laser receiving plate, 31. supporting frame, 32. substrate, 33. adjusting screw, 34. supporting leg, 4. transparent rock specimen, 5. computer.

DETAILED DESCRIPTION OF THE INVENTION

Figure 1:
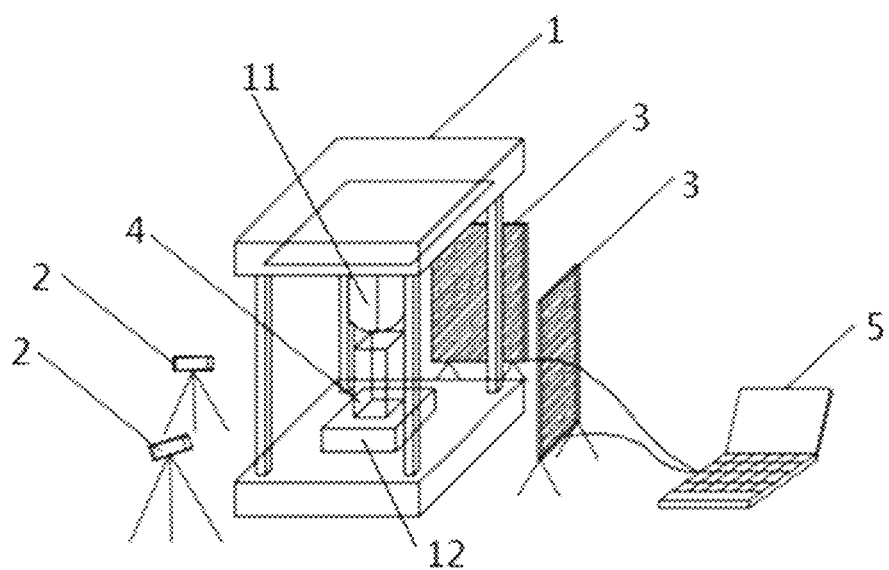
FIG. 1 is a schematic layout diagram of a system for monitoring crack propagation of a transparent rock specimen according to an example of the present invention.
Figure 2:
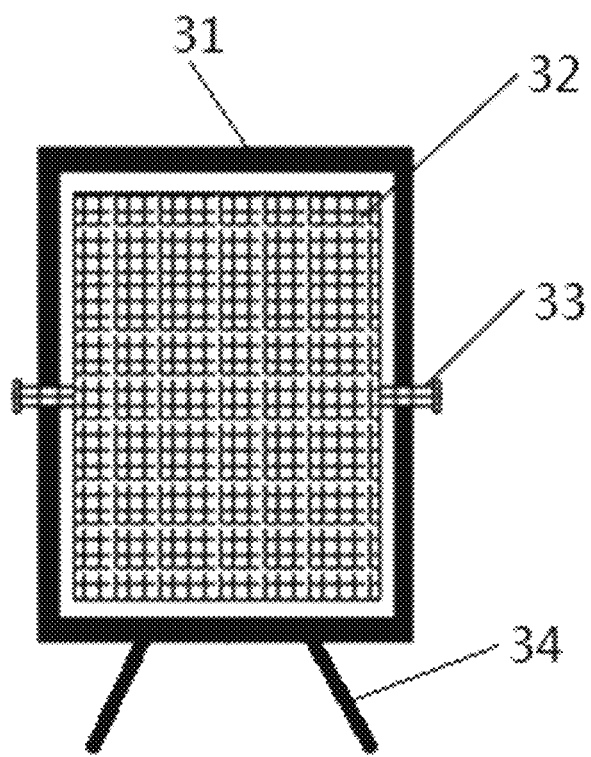
FIG. 2 is a schematic structural diagram of a laser receiving plate in a system for monitoring crack propagation of a transparent rock specimen according to an example of the present invention.

As shown in FIGS. 1 and 2, this example provides a system for monitoring crack propagation of a transparent rock specimen, including a uniaxial rock loading device 1, where a lower end of the uniaxial rock loading device 1 is provided with a loading base 12, a transparent rock specimen 4 is placed on the loading base 12, and a loading head 11 of the uniaxial rock loading device 1 is arranged over the transparent rock specimen 4. After the uniaxial rock loading device 1 is started, the loading head 11 runs downwards, and the loading head 11 and the loading base 12 squeeze the transparent rock specimen 4 between them, so as to perform uniaxial compression tests on the transparent rock specimen 4.

The transparent rock specimen 4 in this example is composed of epoxy resin adhesives A and B and aggregate PMMA particles by mixing. The mixed epoxy resin adhesives A and B and aggregate PMMA particles are poured into a corresponding mold for solidification, demolding and curing to form the transparent rock specimen 4.

The system for monitoring crack propagation of a transparent rock specimen further includes laser emitters 2, laser receiving plates 3 and a computer 5. The laser emitters 2 are used for emitting laser light to the transparent rock specimen 4. The laser light passes through the transparent rock specimen 4 and then is received by the laser receiving plates 3. The laser light irradiates each photosensitive sensor of the laser receiving plates 3. The computer 5 acquires laser intensity data through the photosensitive sensors and processes the data.

The laser emitter 2 is a class Ma laser product. The laser emitter 2 includes a plurality of laser emission sources, and laser light emitted by the plurality of laser emission sources forms a laser beam which can cover the transparent rock specimen 4, so that the laser light can pass through the whole transparent rock specimen 4.

The laser receiving plate 3 includes a substrate 32, a supporting frame 31 and supporting legs 34. A lower end of the supporting frame 31 is provided with the supporting legs 34, so that the supporting frame 31 is supported on a side of the uniaxial rock loading device 1. The substrate 32 is hinged in the supporting frame 31, and a plurality of photosensitive sensors are uniformly arranged on the substrate 32. The supporting frame 31 is provided with an adjusting screw 33, and a tail end of the adjusting screw 33 can press or be separated from the substrate 32 by rotating the adjusting screw 33. The computer 5 is in signal connection with the photosensitive sensors on the laser receiving plates 3.

A laser emitter 2 is separately arranged at a left side and a front side of the uniaxial rock loading device 1; a laser receiving plate 3 is separately arranged at a right side and a rear side of the uniaxial rock loading device. Laser light emitted by the laser emitter 2 passes through the transparent rock specimen 4 and irradiates the photosensitive sensors of the substrate 32 of the laser receiving plate 3. A direction of the laser light emitted by the laser emitter 2 is perpendicular to a surface of the laser receiving plate 3.

This example further provides a method for monitoring crack propagation of a transparent rock specimen, which applies the foregoing system for monitoring crack propagation of a transparent rock specimen according to this example. The method includes the following steps.

Step 1: Mix epoxy resin adhesives A and B and aggregate PMMA particles in different proportions according to experimental requirements, pour the mixture into a corresponding mold for solidification, demolding and curing to form a transparent rock specimen 4, place the transparent rock specimen 4 on a loading base 12 of a uniaxial rock loading device 1, arrange a laser emitter 2 separately at a left side and a front side of the uniaxial rock loading device 1, arrange a laser receiving plate 3 separately at a right side and a rear side of the uniaxial rock loading device, and connect the laser receiving plate 3 with a computer 5.

Step 2: Align an emitting end of each laser emitter 2 with the transparent rock specimen 4, start the laser emitter 2 to emit laser light to the transparent rock specimen 4, rotate a substrate 32 of each laser receiving plate 3, so that a laser direction is perpendicular to a surface of the substrate 32, and rotate an adjusting screw 33 so that a tail end of the adjusting screw presses the substrate 32.

Step 3: Emit, by the left laser emitter 2, laser light to the transparent rock specimen 4; after the laser light passes through the transparent rock specimen 4, record laser intensity by the right laser receiving plate 3; emit, by the front laser emitter 2, laser light to the transparent rock specimen 4; after the laser light passes through the transparent rock specimen 4, record laser intensity by the rear laser receiving plate 3, and acquire, by the computer 5, initial laser intensity data for the transparent rock specimen 4 in an unloaded state through the two laser receiving plates 3.

Step 4: Start the uniaxial rock loading device 1, uniaxially load the transparent rock specimen 4 by the loading head 11 and the loading base 12, and continuously emit laser light to the transparent rock specimen 4 by the left laser emitter 2 while loading; after the laser light passes through the transparent rock specimen 4, continuously record laser intensity by the right laser receiving plate 3; continuously emit laser light to the transparent rock specimen 4 by the front laser emitter 2; after the laser light passes through the transparent rock specimen 4, continuously record laser intensity by the rear laser receiving plate 3, and continuously acquire, by the computer 5, laser intensity data of the transparent rock specimen 4 in a continuously loaded state through the two laser receiving plates 3.

Figure 3:
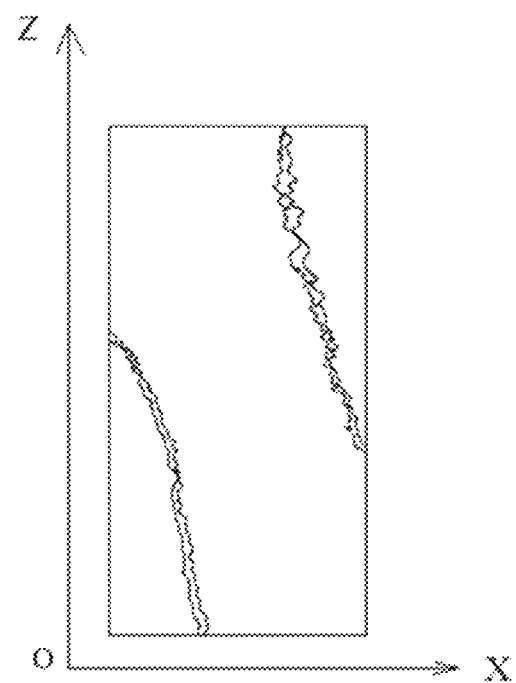
FIG. 3 is a two-dimensional X-0-Z diagram of crack propagation formed in a left-right direction at a certain set time point.
Figure 4:
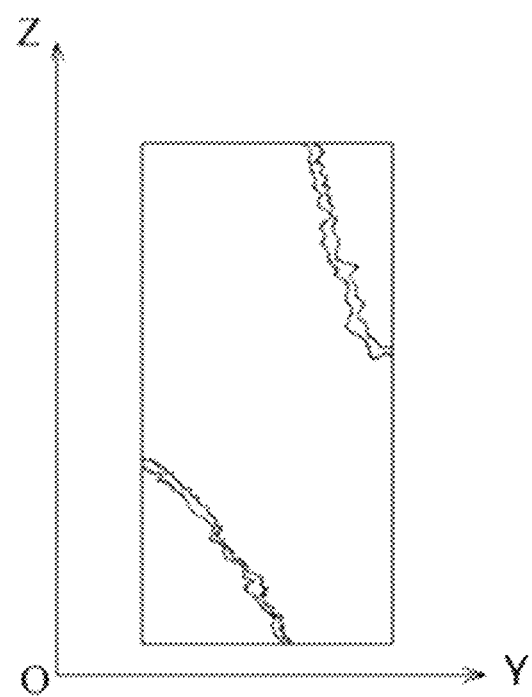
FIG. 4 is a two-dimensional Y-0-Z diagram of crack propagation formed in a front-rear direction at a certain set time point.
Figure 5:
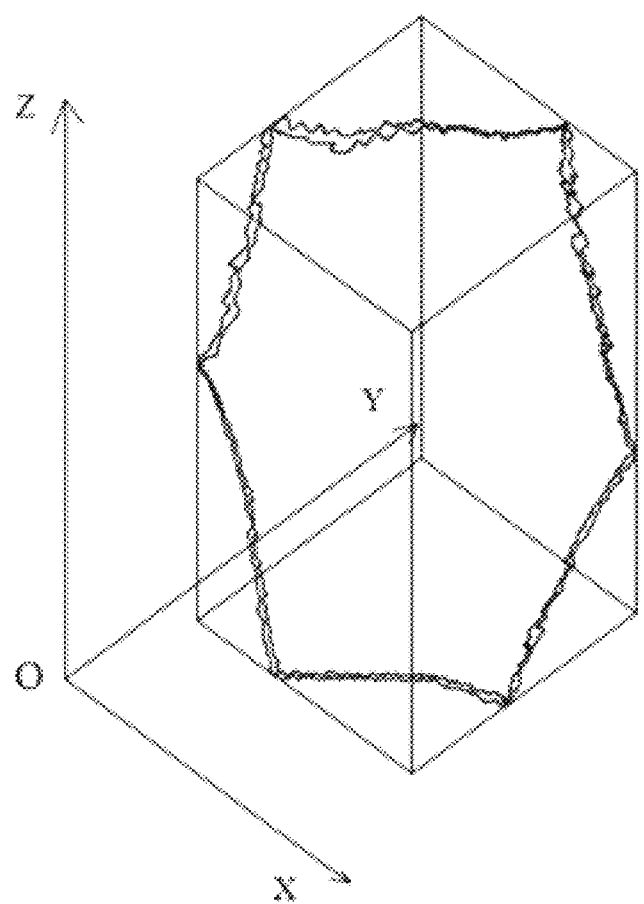
FIG. 5 is a three-dimensional diagram of crack propagation at a certain set time point.

Step 5: According to the acquired initial laser intensity data in the unloaded state and the acquired laser intensity data in the continuously loaded state, process, by the computer 5, to form two-dimensional diagrams of crack propagation of the transparent rock specimen 4 in a continuously loaded state at a plurality of set time points, and synthesize the two-dimensional diagrams of crack propagation into a three-dimensional diagram of crack propagation. FIG. 3 is a two-dimensional X-0-Z diagram of crack propagation formed in a left-right direction at a certain set time point; FIG. 4 is a two-dimensional Y-0-Z diagram of crack propagation formed in a front-rear direction at a certain set time point; and FIG. 5 is a three-dimensional diagram of crack propagation at a certain set time point.

The method for monitoring crack propagation of a transparent rock specimen in this example applies the system for monitoring crack propagation of a transparent rock specimen in this example, under the condition of no contact with a rock specimen, intensity changes of laser light passing through the transparent rock specimen 4 in a loading state are determined, such that a computer 5 forms, according to laser intensity change data, a three-dimensional diagram of crack propagation of the transparent rock specimen 4 in a continuously loaded state at a plurality of set time points. This is used to analyze a breakage starting point and a crack propagation path and process of the transparent rock specimen 4 in the loading state, and achieve the purpose of qualitative analysis of the rock specimen.

Certainly, the above description is not intended to limit the present invention, and the present invention is not limited to the above examples. Changes, modifications, additions or replacements made by those skilled in the art within the essential range of the present invention should fall within the protection scope of the present invention.

What is claimed is:

1. A system for monitoring crack propagation of a transparent rock specimen, the system comprising:
   a uniaxial rock loading device, wherein a transparent rock specimen is arranged on a loading base of the uniaxial rock loading device, and a loading head of the uniaxial rock loading device is arranged above the transparent rock specimen;
   two laser emitters separately arranged at a left side and a front side of the uniaxial rock loading device, wherein the two laser emitters emit a laser light to the transparent rock specimen;
   two laser receiving plates separately arranged at a right side and a rear side of the uniaxial rock loading device, wherein the two laser receiving plates receive the laser light emitted by the two laser emitters;
   a direction of the laser light emitted by each laser emitter is perpendicular to a surface of the one of the laser receiving plates, and the laser light passes through the transparent rock specimen; and
   the computer is in signal connection with the two laser receiving plates, wherein the computer acquires and process a laser intensity data.

2. The system for monitoring crack propagation of a transparent rock specimen according to claim 1, wherein each laser receiving plate comprises a substrate, a plurality of photosensitive sensors uniformly arranged on the substrate, and the computer is in signal connection with the photosensitive sensors.

3. The system for monitoring crack propagation of a transparent rock specimen according to claim 2, wherein each laser receiving plate further comprises a supporting frame, the substrate is hinged in the supporting frame, the supporting frame is provided with an adjusting screw, and a tail end of the adjusting screw is configured to press or be separated from the substrate by rotating the adjusting screw.

4. The system for monitoring crack propagation of a transparent rock specimen according to claim 1, wherein each laser emitter comprises a plurality of laser emission sources, and the laser light emitted by the plurality of laser emission sources forms a laser beam which covers the transparent rock specimen.

5. The system for monitoring crack propagation of a transparent rock specimen according to claim 1, wherein the transparent rock specimen is composed of epoxy resin adhesives and polymethyl methacrylate (PMMA) particles by mixing.

6. A method for monitoring crack propagation of a transparent rock specimen, the method comprising:
   placing a transparent rock specimen on a loading base of a uniaxial rock loading device;
   arranging two laser emitters separately at a left side and a front side of the uniaxial rock loading devices;
   arranging two laser receiving plates separately at a right side and a rear side of the uniaxial rock loading device;
   connecting each laser receiving plate with a computer;
   aligning an emitting end of each laser emitter with the transparent rock specimen;
   starting the laser emitters to emit a laser light to the transparent rock specimen;
   rotating a substrate of each laser receiving plate, so that a laser direction is perpendicular to a surface of the substrate;
   rotating an adjusting screw so that a tail end of an adjusting screw presses the substrate of each laser receiving plate;
   emitting, by the left laser emitter, the laser light to the transparent rock specimen;
   after the laser light passes through the transparent rock specimen, recording a laser intensity by the right laser receiving plate;
   emitting, by the front laser emitter, the laser light to the transparent rock specimen;
   after the laser light passes through the transparent rock specimen, recording the laser intensity by the rear laser receiving plate;
   acquiring, by the computer, an initial laser intensity data for the transparent rock specimen in an unloaded state through the two laser receiving plates;

starting the uniaxial rock loading device, uniaxially loading the transparent rock specimen by the loading head and the loading base;

continuously emitting laser light to the transparent rock specimen by the left laser emitter while loading;

after the laser light passes through the transparent rock specimen, continuously recording laser intensity by the right laser receiving plate;

continuously emitting laser light to the transparent rock specimen by the front laser emitter;

after the laser light passes through the transparent rock specimen, continuously recording the laser intensity by the rear laser receiving plate;

continuously acquiring, by the computer, the laser intensity data of the transparent rock specimen in a continuously loaded state through the two laser receiving plates; and according to the acquired initial laser intensity data in the unloaded state and the acquired laser intensity data in the continuously loaded state, processing, by the computer, to form a three-dimensional diagram of crack propagation of the transparent rock specimen at a plurality of set time points in the continuously loaded state.

7. The method for monitoring crack propagation of a transparent rock specimen according to claim 6, wherein each laser receiving plate comprises a substrate, a plurality of photosensitive sensors uniformly arranged on the substrate, and the computer is in signal connection with the photosensitive sensors.

8. The method for monitoring crack propagation of a transparent rock specimen according to claim 7, wherein each laser receiving plate further comprises a supporting frame, the substrate is hinged in the supporting frame, the supporting frame is provided with the adjusting screw, and the tail end of the adjusting screw is configured to press or be separated from the substrate by rotating the adjusting screw.

9. The method for monitoring crack propagation of a transparent rock specimen according to claim 6, wherein each laser emitter comprises a plurality of laser emission sources, and the laser light emitted by the plurality of laser emission sources forms a laser beam which covers the transparent rock specimen.

10. The method for monitoring crack propagation of a transparent rock specimen according to claim 6, wherein the transparent rock specimen is composed of epoxy resin adhesives and polymethyl methacrylate (PMMA) particles by mixing.

11. A method for monitoring crack propagation of a transparent rock specimen, the method comprising:

placing a transparent rock specimen on a loading base of a uniaxial rock loading device, wherein a loading head of the uniaxial rock loading device is arranged above the transparent rock specimen, two laser emitters are separately positioned at a left side and a front side of the uniaxial rock loading device, each laser emitter is aligned with the transparent rock specimen, two laser receiving plates are separately positioned at a right side and a rear side of the uniaxial rock loading device, and each laser receiving plate is positioned perpendicular to a laser direction of one of the laser emitters and is connected to a computer;

emitting a laser light from each laser emitter to the transparent rock specimen;

acquiring an initial laser intensity data for the transparent rock specimen in an unloaded state from each laser receiving plate using the computer;

uniaxially loading the transparent rock specimen by the loading head and the loading base of the uniaxial rock loading device and continuously acquiring a laser intensity data of the transparent rock specimen in a continuously loaded state from each laser receiving plate by the computer; and forming a three-dimensional diagram of a crack propagation of the transparent rock specimen at a plurality of set time points in the continuously loaded state by processing the acquired initial laser intensity data in the unloaded state and the acquired laser intensity data in the continuously loaded state using the computer.

12. The method for monitoring crack propagation of a transparent rock specimen according to claim 11, wherein each laser receiving plate comprises a substrate, a plurality of photosensitive sensors uniformly arranged on the substrate, and the computer is in signal connection with the photosensitive sensors.

13. The method for monitoring crack propagation of a transparent rock specimen according to claim 12, wherein each laser receiving plate further comprises a supporting frame, the substrate is hinged in the supporting frame, the supporting frame is provided with an adjusting screw, and a tail end of the adjusting screw is configured to press or be separated from the substrate by rotating the adjusting screw.

14. The method for monitoring crack propagation of a transparent rock specimen according to claim 11, wherein each laser emitter comprises a plurality of laser emission sources, and the laser light emitted by the plurality of laser emission sources forms a laser beam which covers the transparent rock specimen.

15. The method for monitoring crack propagation of a transparent rock specimen according to claim 11, wherein the transparent rock specimen is composed of epoxy resin adhesives and polymethyl methacrylate (PMMA) particles by mixing.

* * * * *